(12) United States Patent
Zaghetto et al.

(10) Patent No.: US 8,251,982 B2
(45) Date of Patent: Aug. 28, 2012

(54) LASER APPARATUS FOR THERAPEUTIC APPLICATIONS

(75) Inventors: Lucio Zaghetto, Camposanpiero (IT); Roberto Marchesini, Schio (IT)

(73) Assignee: ASA s.r.l., Arcugnano (IT)

( * ) Notice: Subject to any disclaimer, the term of this patent is extended or adjusted under 35 U.S.C. 154(b) by 1649 days.

(21) Appl. No.: 11/404,099

(22) Filed: Apr. 14, 2006

(65) Prior Publication Data

US 2007/0244526 A1    Oct. 18, 2007

(51) Int. Cl.
*A61N 5/067*    (2006.01)

(52) U.S. Cl. .......................................... 606/2

(58) Field of Classification Search ............... 606/2–19; 607/88–95
See application file for complete search history.

(56) References Cited

U.S. PATENT DOCUMENTS

| | | | |
|---|---|---|---|
| 5,445,146 A | 8/1995 | Bellinger | 607/89 |
| 5,628,744 A * | 5/1997 | Coleman et al. | 606/12 |
| 6,514,241 B1 * | 2/2003 | Hsia et al. | 606/6 |
| 6,554,824 B2 * | 4/2003 | Davenport et al. | 606/3 |
| RE38,670 E * | 12/2004 | Asah et al. | 606/9 |

OTHER PUBLICATIONS

Karu, "Lower-Power Laser Therapy," *Biomedical Photonics Handbook*, Chapter 48, pp. 1-25, CRC Press (2003).
Karu, "Photobiology of Low Power Laser Effects," *Health Phys.* 56(5): 691-704 (1989).
Pagnutti, *Scientific Report, MLS Therapy*, ASA Srl, Arcugnano, Italy (2004).

\* cited by examiner

*Primary Examiner* — Aaron Roane
(74) *Attorney, Agent, or Firm* — Banner & Witcoff, Ltd.

(57) ABSTRACT

Apparatuses and methods for applying laser energy for therapeutic purposes (e.g., relief of pain and/or inflammation in tissues) are disclosed. The synchronization of two spatially overlapping energy forms having closely positioned emission axes and particular emission modalities can in many cases provide strengthened or even synergistic effects in the alleviation or treatment of multiple of acute and/or chronic conditions (e.g., pain and inflammation) afflicting a given tissue. The laser energy forms are characterized in terms of their power levels, activation times, activation periods, pulse durations, pulse periods, wavelengths, and other identified characteristics.

22 Claims, 9 Drawing Sheets

LASER APPARATUS FOR THERAPEUTIC APPLICATIONS

FIELD OF THE INVENTION

The present invention relates to apparatuses and methods for applying laser energy for therapeutic purposes, e.g., relief of pain and/or inflammation in tissues. Effective treatment is achieved through the simultaneous and often synchronized application of at least two laser energy forms that may be spatially overlapping, by virtue of their closely positioned emission axes. Other laser emission parameters described herein for the relief of pain and/or reduction of inflammation in tissues include the power levels, activation times, activation periods, pulse durations, pulse periods, wavelengths and other characteristics of the laser energy forms used.

BACKGROUND OF THE INVENTION

Lasers are recognized as controllable sources of radiation that is relatively monochromatic and coherent (i.e., has little divergence). Laser energy is applied in an ever-increasing number of areas in diverse fields such as telecommunications, data storage and retrieval, entertainment, research, and many others. In the area of medicine, lasers have proven useful in surgical and cosmetic procedures where a precise beam of high energy radiation causes localized heating and ultimately the destruction of unwanted tissues. Such tissues include, for example, subretinal scar tissue that forms in age-related macular degeneration (AMD) or the constituents of ectatic blood vessels that constitute vascular lesions (e.g., portwine stain birthmarks).

Medical uses of lasers also extend into non-destructive or therapeutic methods (i.e., phototherapy). In these methods, photochemical processes are stimulated in selected tissues. Phototherapy is based on the energy requirements of living cells for normal metabolism and repair. The addition of energy directly to damaged tissues can aid in the return of normal function. In particular, laser therapy (which includes the art recognized terms low energy laser therapy (LELT) and low reactive level laser therapy (LLLT)) can promote healing or desired aesthetic changes (e.g., a reduction in swelling) in targeted tissues, such as damaged muscles and tendons that are often afflicted by pain and/or inflammation.

On cellular and molecular levels, the above therapeutic effects are believed to stem from the ability of chromophores (photoreceptive tissue components) to absorb energy at particular wavelengths. This in turn can initiate or enhance a number of possible biological mechanisms including cell replication, cell metabolism, protein synthesis, adenosine triphosphate (ATP) production, mitochondria replication, phagocytosis, and photodissociation of oxygenated hemoglobin. See Karu, T., THE SCIENCE OF LOW-POWER LASER THERAPY, Gordon and Breach, 1998. Proposed tissue-related activities associated with light absorption include capillary formation, parasympathetic nervous system stimulation, increased endorphin release, increased production and release of adrenal steroids, reduction in pain and in inflammation, reduction of tissue edema, immune system stimulation, enhanced fibroblastic production and collagen synthesis, and accelerated healing of wounds. See Karu, T., *Photobiology of Low Power Laser Effects*, HEALTH PHYS. May; 56(5): 691-704 (1989).

Therapeutic benefits result from the activation of different photoreceptors that respond to different wavelengths. The energy absorbed by a given tissue depends on the photoreceptive components present, relative to the wavelength used. The absorption of energy by some constituents of virtually all tissues is also a consideration in designing treatment protocols. This is particularly true for therapies (e.g., those involving muscle or joint tissue) where energy must be delivered a significant depth below the skin surface. Water and hemoglobin, for example, are known to absorb specific infrared and visible light wavelengths, respectively, which therefore do not easily penetrate far into the body. The ability of tissues to reflect, absorb, or scatter particular wavelengths at or near the site of energy application also impacts the dose versus depth relationship.

BRIEF SUMMARY OF THE INVENTION

Embodiments of the present invention are directed to methods of treating pain and/or inflammation in tissues in need of such treatment using laser light. While conventional phototherapy developments have primarily involved the optimization of wavelength, a number of other parameters relating to the energy form(s) applied can also impact performance. In cases where two or more separate laser energy forms are used, these parameters include the relative positioning their emission axes and/or the spatial relationship of their emission beams, as well as the selection of continuous, periodic, or pulsed laser energy (or combinations of these). Other considerations include the synchronization of two or more forms of laser energy and the relative power levels of these energy forms. Ideally, different energy forms can be used in the simultaneous treatment of multiple conditions (e.g., pain and inflammation) associated with the tissue undergoing phototherapy.

The present invention is based on the realization that the use of two or more laser energy forms having closely positioned emission axes and/or spatial overlap, in combination with certain emission modalities, increases phototherapeutic effectiveness. The synchronization of two energy forms can provide synergistic effects in the alleviation or treatment of multiple acute and/or chronic conditions such as pain and inflammation afflicting a given tissue. With respect to periodic or pulsed energy forms, parameters for consideration in achieving the desired effect of phototherapy include the power level, activation time (or "on time"), activation period, pulse duration, and pulse period (as well as the duration and period of trains of pulses). Also associated with the present invention is the provision of apparatuses for applying at least two laser energy forms, having a desired spacing between their respective emission axes, which may provide overlapping emission beams, simultaneously to a treatment zone such as a tendon or muscle in need of such treatment. The therapeutic effect may be enhanced through the use of desired emission modalities of these laser energy forms. For purposes of discussion, the treatment zone is the area or volume of tissue which receives the incident laser light.

In one embodiment, the present invention is a method of delivering laser energy to a treatment zone. The method comprises simultaneously applying a first laser energy form and a second laser energy form to the treatment zone. Preferably, the first and second laser energy forms have emission axes that are spaced apart by at most about 1 mm. In other embodiments, the emission axes are spaced apart by at most about 0.5 mm or at most about 0.2 mm. By virtue of closely spaced emission axes, the first and second laser energy forms may, in preferred embodiments, spatially overlap over most of the lengths of their respective emission axes, and often over at least about 90% of these lengths. In terms of emission modalities, the first laser energy form may be applied periodically with a first activation time ($t^1_{on}$) and a first activation period ($T^1$), to the treatment zone. The second laser energy form may be applied either continuously or periodically to the treatment zone. During the first activation time ($t^1_{on}$), a plurality of laser energy pulses are applied with a pulse duration ($t^1_{pulse}$) and a pulse period ($T^1_{pulse}$). Typical ranges for the first activation time ($t^1_{on}$), the pulse duration ($t^1_{pulse}$), and pulse period ($T^1_{pulse}$) are from about 100 to about 1000 microseconds, from about 5 to about 500 nanoseconds, and from about 5 to about 500 microseconds, respectively. Representative wavelengths for each of the first and second laser energy forms are from about 600 to about 1100 nanometers.

In another embodiment, the pulses of the first laser energy form have a power ($P^1$) and the second laser energy form has a power ($P^2$), with $P^1 > P^2$. Typical values of $P^1$ and $P^2$ range from about 10 to about 100 watts and from about 1 to about 6 watts, respectively. The second laser energy form may be emitted continuously or periodically with a second activation time ($t^2_{on}$) and a second activation period ($T^2$). In the case of periodic emission of the second laser energy form, the second activation period ($T^2$) may be equal to or substantially equal to the first activation period ($T^1$). For substantially equal activation periods, the first and second laser energy forms may be synchronized by setting the first activation time ($t^1_{on}$) and the second activation time ($t^2_{on}$) to begin simultaneously or substantially simultaneously.

The methods described above may be used in alleviating or treating various conditions, including those characterized by pain, inflammation, or edema of tissues such as tendons or muscles. Representative applications include, but are not limited to, the alleviation or treatment of rheumatic disorders, sport traumas, joint pain (e.g., shoulder pain), or lesions. Other particular conditions include pain and/or inflammation associated with contusions, hematomas, distortions, muscle strains, lumbago, sciatalgia, myositis, epicondylitis, synovitis, bursitis, or capsulitis.

In another embodiment, the present invention is an apparatus for performing any of the methods described above. A representative apparatus comprises a control unit for controlling the operation of a first laser and a second laser. These lasers may, in a representative embodiment, be positioned within an optical unit such that distance between their emission axes is small, with typical separations between emission axes as described above. The close positioning of emission axes may result in overlap of the emission beams immediately upon exiting either of both of the first and second lasers. In particular embodiments, the first laser emits periodically a first radiation form, having a first activation time ($t^1_{on}$) and a first activation period ($T^1$), to a treatment zone. The second laser emits, preferably simultaneously with the first laser and either continuously or periodically, a second radiation form to the treatment zone. Over the first activation time ($t^1_{on}$), a plurality of radiation pulses are emitted with a pulse duration ($t^1_{pulse}$) and a pulse period ($T^1_{pulse}$). The apparatus may further comprise other components including a user interface for receiving operating parameters and inputting these parameters into a command unit. In this case, the control unit controls the operation of the first laser and the second laser based on output from the command unit.

These and other embodiments are apparent from the following Detailed Description.

The features of the apparatuses and energy forms referred to in the above FIGS. 1-7 are not necessarily drawn to scale and should be understood to present an illustration of the invention and/or principles involved. Some features depicted in the figures have been enlarged or distorted relative to others, in order to facilitate explanation and understanding. The same reference numbers are used in the figures for similar or identical components or features shown in the various embodiments. Laser devices, as disclosed herein, will have configurations, components, and operating parameters determined, in part, by the intended application and also the environment in which they are used.

DETAILED DESCRIPTION OF THE INVENTION

The present invention is directed to the use of at least two laser energy forms (e.g., continuous, periodic, and/or pulsed emissions) with closely coupled emission axes to deliver a number of possible therapeutic benefits to tissues in need thereof. Continuous energy emission refers to a constant or substantially constant emission of laser energy over time. The term "substantially constant" in reference to an energy emission indicates that the power level of the emission varies over an uninterrupted emission time or activation time generally by at most about 10%, typically by at most about 5%, and often by at most about 1%.

Periodic energy emission refers to constant or substantially constant laser energy emissions, as defined above, that are interrupted at regular or substantially regular time intervals.

The term "substantially regular" in reference to time intervals in which energy emissions are interrupted indicates that the time intervals differ by at most about 10%, typically by at most about 5%, and often by at most about 1%. These time intervals, for example, may be on the order of hundreds of microseconds.

Pulsed energy emission refers to laser energy emissions in very rapid succession, with pulse durations typically lasting hundreds of nanoseconds. Pulsed emissions are constant or substantially constant, as defined above, from one pulse to the next, over an uninterrupted emission time or activation time in which a plurality of pulses are emitted. A "pulse train" or "train of pulses" refers to the periodic emission, as defined above, of pulsed energy.

Two or more laser energy forms may be applied to a treatment zone, such that these energy forms spatially overlap over some or all of the length of their respective emission axes (from the region of emission from laser sources to a region of the tissue that is targeted for phototherapy). Normally, the laser energy forms similarly overlap at an area on the surface of the skin, through which the emission beams may penetrate in order to reach an underlying tissue that is targeted for treatment. In a typical case where spatial overlap of the emission beams is achieved both at the skin surface, where they are introduced into the body, and at a different, targeted tissue, the emission axes of two lasers are generally positioned in close proximity. For example, the respective emission axes of the two or more laser energy forms may be spaced apart generally by at most about 1 mm, typically by at most about 0.5 mm, and often by at most about 0.2 mm. The emission axes may be coincident, in which case they have no separation, or they may otherwise have a slight offset, such that they are separated or spaced apart (e.g., in a parallel relationship), for example, from about 0.01 mm to about 1 mm, from about 0.05 mm to about 0.5 mm, or from about 0.1 mm to about 0.2 mm. The above distances may refer to the coincidence or offset between the emission axes, as measured at a point close to the laser sources (e.g., at the emission beam outlet of one or both of two lasers). These separations between emission axes may also generally be maintained over most of the lengths of one or more (e.g., one or both of two) emission axes, such that the emission beams of the lasers spatially overlap over these distances. Often, the laser energy forms will spatially overlap over at least about 90% of the length of one or more of the emission axes, or even over substantially the entire length of the emission axes. This results in a close coupling of the emission axes of the two or more laser energy forms, which provides benefits in phototherapy, as discussed herein.

The length of an emission axis is the distance from the source of the laser energy emission to the treatment zone to which the energy is applied. Typical emission axes will have lengths ranging from about 0.5 to about 50 cm, often from about 5 to about 25 cm. In alternative embodiments (e.g., for the treatment of surface tissues such as swelling and/or sores on the skin), a laser emitting device according to the present invention may be contacted directly with the target tissue, such that the emission axis length is essentially 0. Generally, in accordance with the present invention, laser energy forms can overlap immediately upon exiting their respective sources (e.g., laser emitting diodes). In some embodiments, the laser energy sources may be positioned such that their respective emission axes are closely coupled or even coincident as discussed above, but these sources may nevertheless be at somewhat different distances from the treatment zone (e.g., one diode laser being positioned slightly closer to the treatment zone than another diode laser). In such cases, overlap of two emission beams upon exit from their respective lasers means that the laser energy forms begin to overlap where the closer of the two lasers (either the first or the second laser) emits.

The treatment zone, or region of intersection of the emission beams at the targeted tissue, may have a cross-sectional area on the surface of this tissue that defines a treatment area. This treatment area is generally from about 0.5 to about 500 $cm^2$, typically from about 1 to about 250 $cm^2$, and often from about 1 to about 100 $cm^2$. In embodiments where a laser emitting device is contacted directly with the skin as described above, treatment areas can often be in the range from about 1 to about 50 $cm^2$. For example, a treatment spot of about 2 cm in diameter (about 3 $cm^2$ in area) has been found particularly effective in such cases.

Many treatment area shapes are possible and are dictated by the cross sectional areas of laser energy forms. For example, two laser beams having circular cross sectional beams may have an area of intersection at the treatment zone that defines a circular or possibly a lens-shaped treatment area. The use of differing beam diameters may also allow for a "hot spot" treatment area of intersecting energy, surrounded by a peripheral area of lower intensity. More complex treatment areas are possible with the use of three or more emission beams that intersect at the treatment zone. Various conventional optical devices such as spot shaping lenses or line generating prisms may be used to change the cross-sectional shape of one or more of the beams, in order to shape the treatment area as desired. Adjustment of the distance between the laser sources and the treatment zone may also be used to change the size and/or shape of the treatment area and/or treatment zone.

Preferred wavelengths of the energy forms used in the apparatuses and treatment methods described herein are in the range generally from about 600 to about 1100 nanometers (nm), about 700 to about 1100 nm, and often from about 800 to about 1000 nm. These wavelengths normally apply to each of the two or more laser energy sources used. The absorption of energy by photoreceptive components (e.g., water, hemoglobin, and melanin) at the skin surface is generally reduced in most of this "therapeutic window" of wavelengths, allowing more effective delivery of the energy to deeper tissue layers. It is often desirable to use different wavelengths within this range for spatially overlapping laser energy sources. For example, a first laser energy form may be a pulsed emission at 905 nm to provide an analgesic effect, while a second overlapping laser energy form may be a continuous emission at 808 nm to provide an anti-inflammatory or anti-edema effect. Synchronization of these energy forms, as described herein, can be employed to strengthen and even synergize these therapeutic effects.

The rate of energy, as well as the total energy, delivered per unit area in the non-destructive or therapeutic methods according to the present invention are normally considerably below the quantities used in surgical or even cosmetic applications (e.g., varicose vein treatment). The combined rate of energy applied from the two or more laser energy sources will generally range from about 1 to about 25 $mW/cm^2$, and often from about 5 to about 20 $mW/cm^2$. The absorption of energy at these rates can potentially increase the temperature of the targeted tissue to above the basal body temperature, although not to an extent where thermal damage will occur. The total amount of energy delivered in a typical treatment will generally range from about 0.5 to about 50 $j/cm^2$, and often from about 0.5 to about 20 $j/cm^2$, whereas, in comparison, sclerotherapy for vein treatment will generally require energy densities in the range of 10-50 $j/cm^2$.

Semiconductor or diode lasers represent possible sources of laser energy that may be used, as these components are readily available in varying power/wavelength combinations. Laser emitting diodes also can be used to emit continuous or selectively pulsed radiation in multiple wavelengths. In one embodiment of the invention, a laser emitting diode is the source of each of two overlapping energy forms. Often, however, at least two separate laser sources (e.g., two diode lasers) will be employed, with each operating independently. Other types of lasers known in the art, preferably those that emit radiation in the range of wavelengths discussed above, may also be used. In cases where a particular type of laser emits radiation at both desired and undesired wavelengths, the use of filters, reflectors, and/or other optical components can aid in targeting a tissue with only the desired type of radiation.

Alternative types of lasers include those containing crystal, gas, dye, or other lasing media. A representative known laser operates with a yttrium-aluminum garnet crystal, doped with neodymium (Nd:YAG laser). In a predominant mode of operation, population inversion of $Nd^{+3}$ ions in the YAG crystal causes the emission of a radiation beam at 1064 nm. The Nd:YAG laser can be operated in a pulsed or continuous mode with an adjustable beam energy output. Similarly, neodymium may be used as a dopant of pervoskite crystal (Nd:YAP or Nd:YAlO3 laser) or a yttrium-lithium-fluoride crystal (Nd:YAF laser) to provide lasing media capable of emitting radiation at 1079 nm and 1055 nm, respectively. Other rare earth and transition metal ion dopants (e.g., erbium, chromium, and titanium) and other crystal and glass media hosts (e.g., vanadite crystals such as YVO, fluoride glasses such as ZBLN, and silica glasses) of these dopants may be used as lasing media. Flashlamps or other suitable excitation media may be employed. The above mentioned types of lasers may also emit radiation in the visible region of the electromagnetic spectrum. Ruby and helium-neon lasers, for example, emit radiation at 694 nm and 633 nm, respectively. It is also possible to use a low power beam (e.g., <100 mw) of visible laser light as a guide or alignment tool for one or more of the laser energy forms which provide therapeutic benefits.

Figure 1:
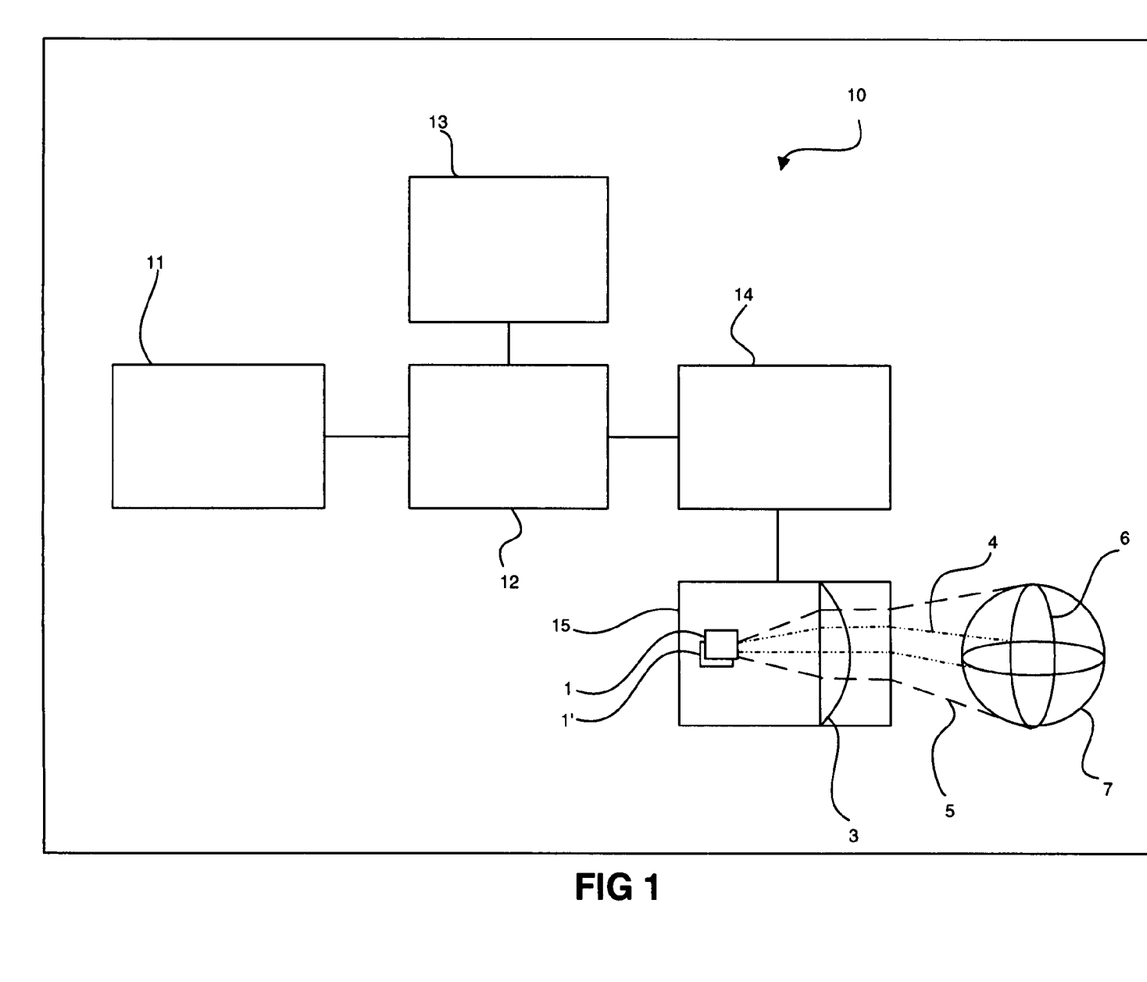
FIG. 1 depicts a representative a laser emitting device for therapeutic applications, as described herein.
Figure 2:
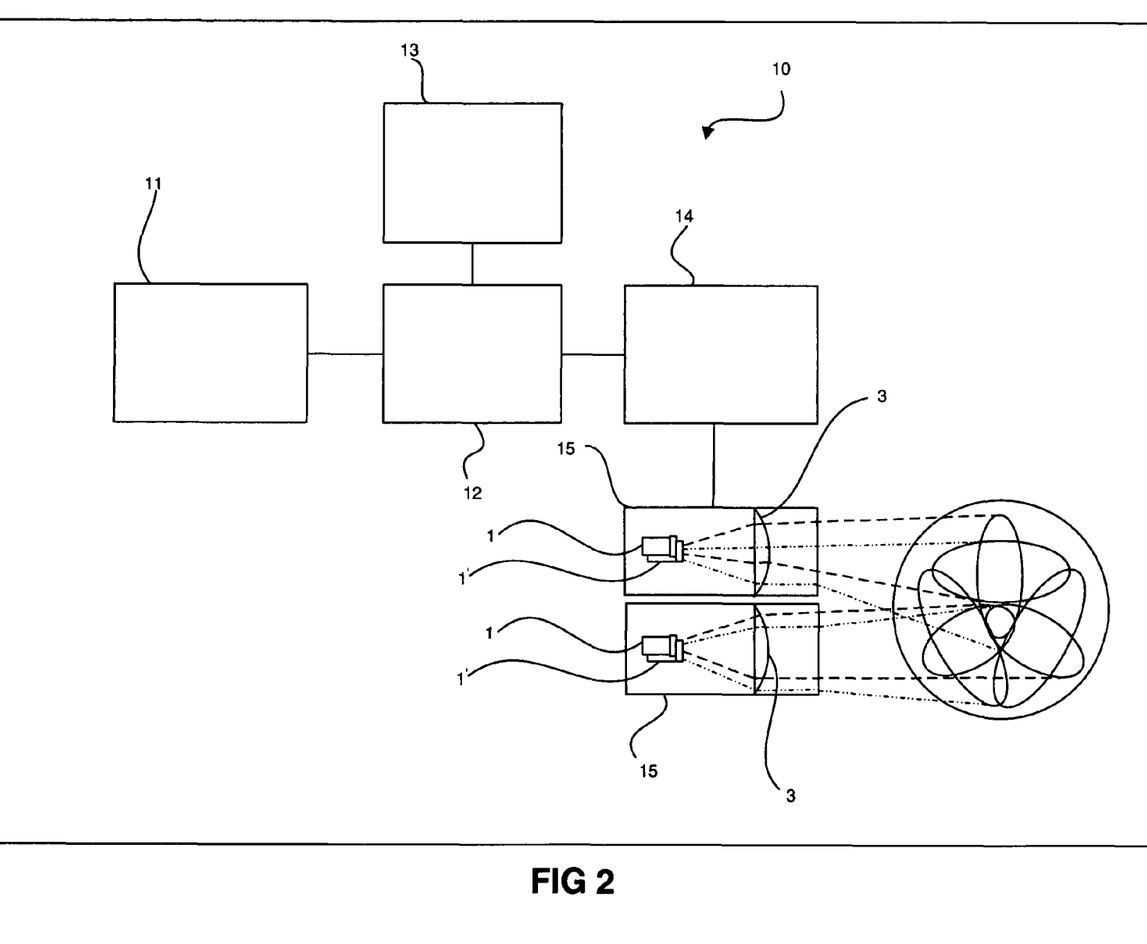
FIG. 2 depicts another representative laser emitting device.

FIGS. 1 and 2 depict in schematic representative embodiments of a laser emitting device 10 for therapeutic applications. In FIGS. 1 and 2, the same reference numbers are used to identify similar or identical components. In these embodiments, a power supply 11 which may be in the form of an energy storage network or battery, or which may be operatively connected to a capacitor bank (not shown) is used as a power source for an optical unit 15 comprising at least two laser sources 1 and 1'. FIG. 2 shows an alternative embodiment where two sets of two laser sources (1 and 1') have closely coupled emission axes and each set is housed in an optical unit 15. In both FIGS. 1 and 2, laser sources 1 and 1' have spatially overlapping emission beams. For example, emission beams 4 and 5 in FIG. 1 overlap to define a spot configuration 6 of a treatment zone 7, having a size and/or shape which may be varied using a lens 3. Also included in FIGS. 1 and 2 is a user interface 13 for the activation and management of the device 10. The user interface 13 receives operating parameters that are input into a command unit 12, which may comprise a microprocessor.

The user interface 13 and command unit 12 may be contained in a local or remote device. The command unit 12 may include software having stored operating protocols or parameter values, suitable for alleviating or treating various disorders, where the software allows a user to select one or more of these protocols through the user interface 13. Stored operating protocols may include, for example, the values for optical power, activation time, activation period, and treatment time for each of two laser sources and additional values for pulse duration and pulse period for one of the two laser sources. The command unit 12 may otherwise or additionally include software that allows a user to input values for various operating parameters, including any or all of those identified above, through the user interface 13.

The command unit 12 interprets operating information entered into the user interface 13 and provides the working parameters of the laser sources 1 and 1' through a control unit 14. Output from the command unit 12 is thus provided to the control unit 14 which may also have a microprocessor (e.g., a central microprocessor) in direct or remote communication with a microprocessor of the command unit 12. The control unit 14 receives the operating parameters from the command unit 12 to control the operation of at least two laser sources 1 and 1' of the optical unit 15, and possibly other components (not shown) of the device 10. For example, the control unit 14 may provide the necessary signals for the operation of excitation flashlamps, synchronizers or timers, switches, and other components, as needed to carry out the operating protocol for the laser sources 1 and 1', as received from the command unit 12. Additional conventional optical components (not shown) may be used in conjunction with device 10, such as shutters or beam attenuators, reflecting prisms or other reflecting components, filters, light focusing components such as concentrators or condensers, collimating lenses, etc.

In the embodiments shown in FIGS. 1 and 2, the laser sources 1 and 1' are positioned close to each other (e.g., with their emission axes separated by at most about 0.2 mm), and their respective emission beams (4 and 5 in FIG. 1) overlap from the region of emission from laser sources 1 and 1' to the region of treatment zone 7 that is targeted for phototherapy. In the embodiment shown in FIG. 2, two sets of two overlapping emission beams from laser sources 1 and 1' intersect in a treatment zone. In one embodiment, laser sources 1 and 1' provide spatially overlapping, yet different and independent, forms of laser energy which are advantageously synchronized, as discussed below, for effective therapy. Synchronization is achieved by software and/or hardware contained in the command unit 12 and also by hardware contained in the control unit 14. Hardware in the command unit 12 and/or control unit 14 may therefore include a synchronizer (not shown) for activating laser sources 1 and 1'.

Devices of the present invention, such as those represented in FIGS. 1 and 2, may be used to apply laser energy at a monitored and/or controlled distance from the treatment zone. Monitoring of the length of the emission axis may be accomplished, for example, using an ultrasound sensor or other measuring device. Distance from the treatment zone may be controlled, for example, using robotized movement of an emission head, which appropriately responds to measured differences in the length of the emission axis.

FIGS. 3 to 7 provide graphical representations of the power of two laser energy forms A and B as a function of time. According to some methods of the present invention, these laser energy forms may have closely positioned emission axes and/or may spatially overlap. The laser energy forms A and B may also intersect at a treatment zone in a targeted tissue to which they are applied. The same reference numbers are used in FIGS. 3 to 7 to identify similar or identical parameters associated with the laser energy forms A and B. These figures illustrate laser energy form emissions occurring over a representative portion of a phototherapy session or treatment in which energy is applied to one or more tissues in a patient. A phototherapy session may represent a one-time administration of energy to a tissue or may be part of an overall phototherapeutic regimen involving a course of treatments designed to alleviate or treat a condition in a patient.

FIGS. 3 to 7 illustrate several of a large number of possible emission modalities according to the present invention, which are readily apparent to one of ordinary skill, having regard for the present disclosure. In particular, activation of a first laser source provides a first laser energy form A, which is emitted as a pulse train. Simultaneous activation of a second laser source provides a second laser energy form B, which is emitted periodically, although in some embodiments the second laser energy form B may also be emitted continuously. In representative embodiments of the invention, short pulses of energy form A may have a relatively high power $P^1$, which generally ranges from about 1 to about 500 watts and often from about 10 to about 100 watts. As illustrated in FIGS. 3 to 7, energy form B preferably is emitted with a power $P^2$ that is less than $P^1$. The value of $P^2$ generally ranges from about 0.5 to about 10 watts and often from about 1 to about 6 watts. The values of $P^1$ and $P^2$ will generally depend on the source size.

Figure 3:
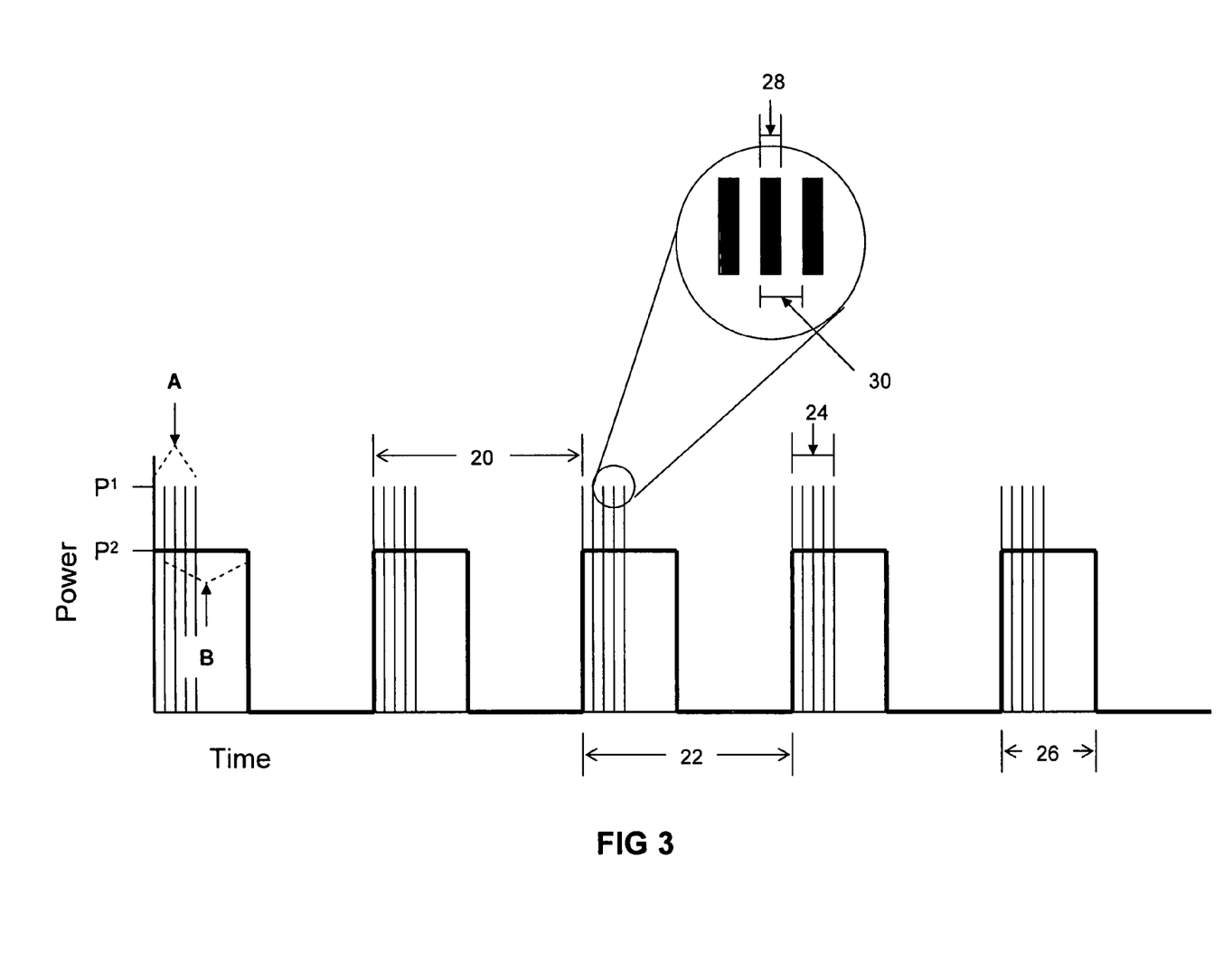
FIG. 3 is a graphical representation of the power of two laser energy forms as a function of time, with a first laser energy form being emitted as a train of pulses and a second laser energy form being emitted periodically. The activation periods for the train of pulses ($T^1$) and the for the second laser energy form ($T^2$) are equal. Also, both laser energy forms are activated simultaneously, with the first activation time being less than the second activation time ($t^1_{on} < t^2_{on}$).
Figure 4:
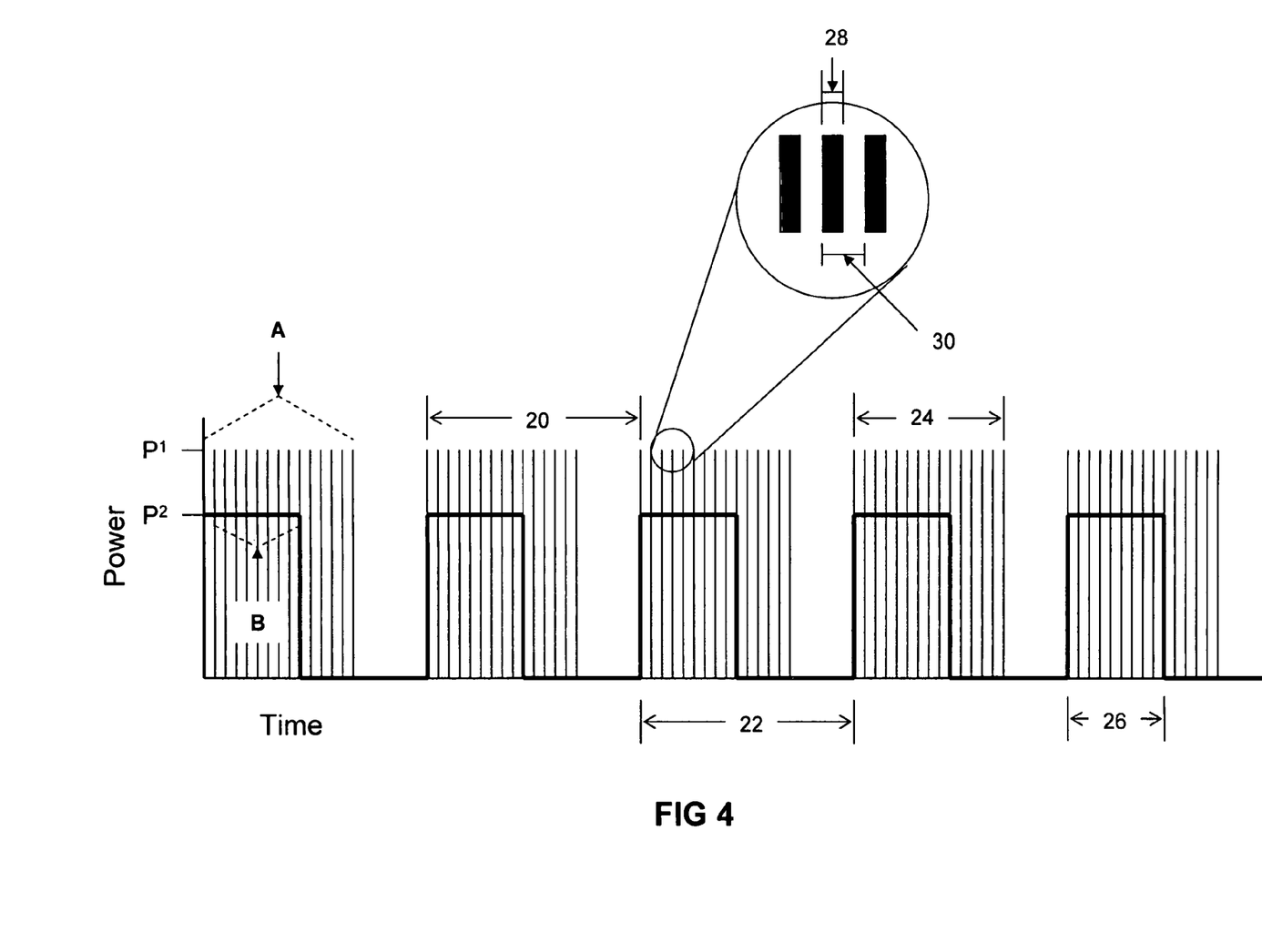
FIG. 4 also graphically represents the power versus time relationship for two laser energy forms, namely a first pulse train emission and a second periodic emission. As in FIG. 3, both laser energy forms are activated simultaneously, but in this case the first activation time is greater than the second activation time ($t^1_{on} > t^2_{on}$).
Figure 5:
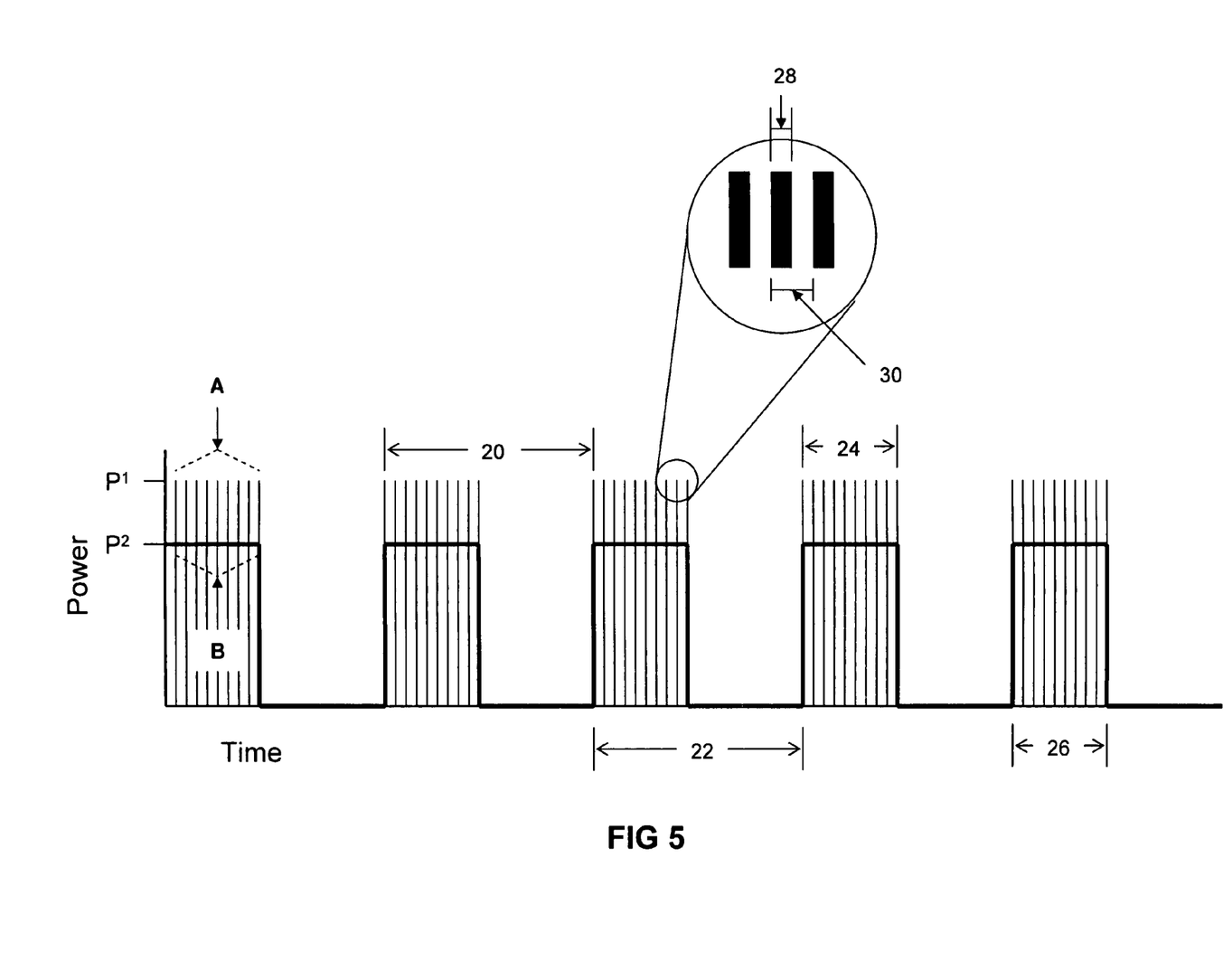
FIG. 5 graphically represents the power versus time relationship for two laser energy forms which are similar to FIG. 4, except that the first activation time is equal to the second activation time ($t^1_{on} = t^2_{on}$).

As is shown in FIGS. 3 to 5, the pulse train of the first energy form A has an activation period 20 ($T^1$), which is the time required to complete one cycle of pulse emissions. Likewise, when the second energy form B is emitted periodically, it also has activation period 22 ($T^2$). In particular embodiments of the invention, these activation periods 20 and 22 are equal or substantially equal, as shown in FIGS. 3 to 5. The term "substantially equal" in reference to activation periods indicates that two energy forms have activation periods differing generally by at most about 10%, typically by at most about 5%, and often by at most about 1%.

Advantageously, the use of equal or substantially equal activation periods 20 and 22 allows for the effective synchronization of the "on" times for energy forms A and B, as shown in FIGS. 3 to 5. Synchronization of pulsed and periodic emissions, according to these particular illustrative embodiments of the invention, provides a strengthened or even synergistic therapeutic effect. For example, the analgesic effect of applying a train of pulses to a tissue may be accelerated at the same time that the anti-inflammatory or anti-edema effect of applying a periodic emission is intensified, if these two emissions are synchronized. In certain embodiments, therefore, when the activation periods 20 and 22 are equal or substantially equal, the time periods in which the first and second energy forms A and B are activated (i.e., the first activation time or duration 24 ($t^1_{on}$) and the second activation time or duration 26 ($t^2_{on}$)) begin simultaneously or substantially simultaneously. The term "substantially simultaneous" in reference to activation of energy forms indicates that two energy forms are activated at times that differ generally by at most about 10%, typically at most about 5%, and often by at most about 1%, of the first or second activation period.

By virtue of the substantially equal activation periods 20 and 22, synchronization of the beginning of the activation times 24 and 26 can be maintained throughout a phototherapy treatment. The substantially simultaneous activation of the first and second energy forms A and B therefore gives a synchronized output that is highly effective in the treatment of body tissues by phototherapy. A synchronization component may be included in the control unit hardware of a laser apparatus to accomplish this result.

FIGS. 3 to 5 graphically depict the output over time of a first laser energy form A being emitted as a train of pulses and a second laser energy form B being emitted periodically. The activation periods for the pulse train 20 ($T^1$) and for the periodic emission 22 ($T^2$) are equal. Also, the laser energy forms are shown as being activated simultaneously. In FIG. 3, the first activation time 24 is less than the second activation time 26 (i.e., $t^1_{on}<t^2_{on}$). However, it is also possible for the first activation time 24 to be greater than the second activation time 26 (i.e., $t^1_{on}>t^2_{on}$) as shown in FIG. 4, or for these activation times 24 and 26 to be equal (i.e., $t^1_{on}=t^2_{on}$), as shown in FIG. 5.

Regardless of the relative values of the activation times $t^1_{on}$ and $t^2_{on}$, their duration will generally range from about 10 to about 5000 microseconds, and often from about 100 to about 1000 microseconds. As shown in FIG. 5, the activation time or duration of the first energy form 24 ($t^1_{on}$) may be about one half of the activation period of the first energy form 20 ($T^1$), and likewise the activation time or duration of the second energy form 26 ($t^2_{on}$) may be about one half of the activation period of the second energy form 22 ($T^2$). These activation times 24 and 26 ($t^1_{on}$ and $t^2_{on}$), however, may independently vary (as shown in FIGS. 3 and 4 with respect to $t^1_{on}$), such that these activation times will generally range from about 10% to about 90%, and often from about 25% to about 75%, of their respective activation periods 20 and 22 ($T^1$ and $T^2$).

Figure 6:
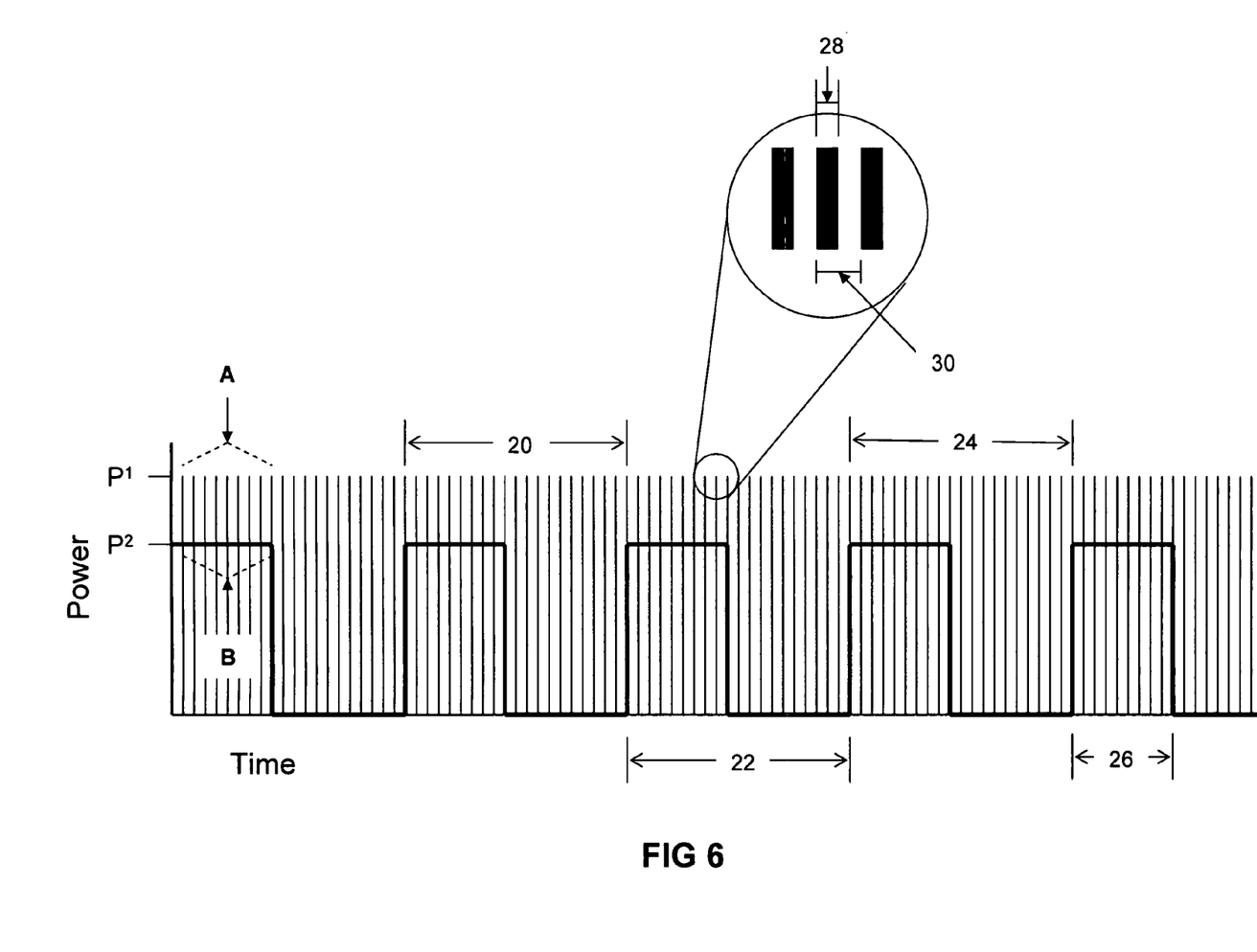
FIG. 6 graphically represents the power versus time relationship for two laser energy forms. In this case, the first activation time ($t^1_{on}$) is equal to the first and second activation periods ($T^1$ and $T^2$) such that the first energy form is emitted as a continuous pulse.
Figure 7:
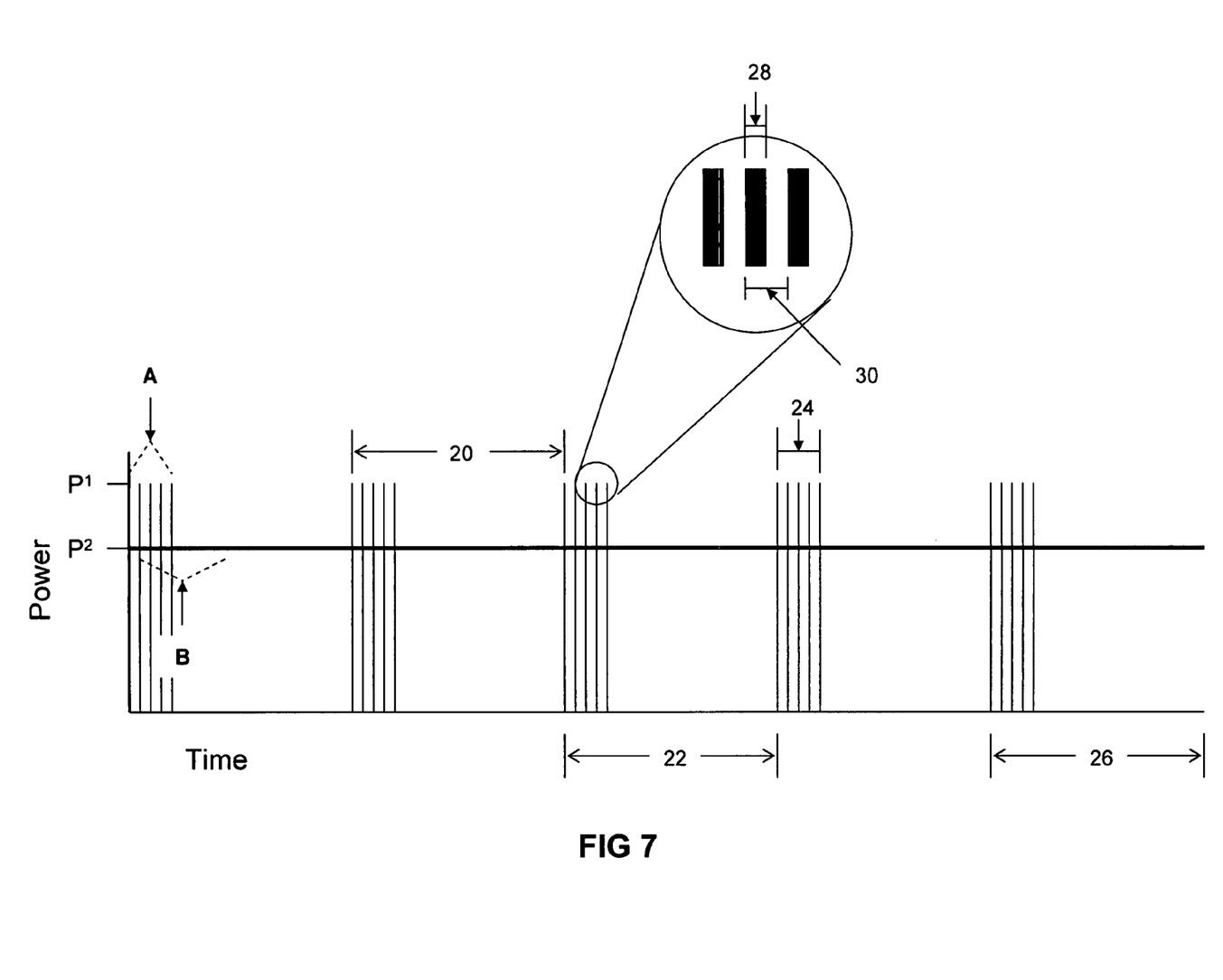
FIG. 7 graphically represents the power versus time relationship for two laser energy forms, where the second energy form is emitted continuously (i.e., the second activation time ($t^2_{on}$) is equal to the first and second activation periods ($T^1$ and $T^2$)).

FIG. 6 represents an embodiment of the invention where two laser energy forms are emitted with the first activation time 24 ($t^1_{on}$) being equal to both the first and second activation periods 20 and 22 ($T^1$ and $T^2$) such that the first energy form A is emitted as a continuous pulse, rather than as a train of pulses, as illustrated in FIGS. 3 to 5. FIG. 7 represents another embodiment of the invention where the second energy form B is emitted continuously (i.e., the second activation time 26 ($t^2_{on}$) is equal to the first and second activation periods 20 and 22 ($T^1$ and $T^2$)). In another embodiment where the second energy form B is emitted continuously or periodically, the first energy form A may be emitted at the same time as a single, non-continuous pulse train. In this case, the first activation period is longer than the time of the phototherapy treatment.

The illustrations in FIGS. 3 to 7 of the various representative emission modalities also include an exploded view to better show the nature of individual pulses of the first energy form A. Each individual pulse therefore has duration 28 ($t^1_{pulse}$), which is normally significantly shorter than the first activation time or duration 24 ($t^1_{on}$), and generally ranges from about 1 to about 1000 nanoseconds, and often from about 5 to about 500 nanoseconds. The values for the pulse period 30 ($T^1_{pulse}$) generally range from about 1 to about 1000 microseconds, and often from about 5 to about 500 microseconds. The above ranges for $t^1_{pulse}$ and $T^1_{pulse}$ correspond, for example, to values obtained in the operation of a typical pulsed diode laser with a duty cycle of about 0.1%. The above ranges for $T^1_{pulse}$ also correspond to a pulse frequency generally ranging from about 1000 Hz to about 1 MHz, and often from about 2000 Hz to about 200 kHz during the activation time 24 ($t^1_{on}$). The goal of any particular phototherapy treatment is to deliver combined laser energy having suitable characteristics (e.g., pulse power, pulse duration, activation time, activation period, etc.) to sufficiently energize the targeted tissue, while avoiding thermal damage to that tissue or surrounding tissues.

The emission modalities discussed above, which can be generated from two sources of laser energy, optionally having closely positioned emissions axes and/or spatial overlap, as well as other characteristics described herein, may be employed in therapy for the treatment of tissues, with a high level of effectiveness. Advantageously, the spatial coordination and/or synchronization of two energy forms can generate a synergized or "high quality" photoemission that provides therapeutic effectiveness which could not otherwise be achieved using the relatively low overall power levels applied. Spatial coordination, resulting from closely positioned emission axes and/or spatial overlap of energy forms, can provide uniform coverage of a treatment area in terms of both the intensity and type of radiation received. This in turn helps ensure uniform activation of photoreceptive tissue components in that treatment area. Moreover, spatial coordination can minimize losses of laser energy due to the comparatively greater extent of reflection and scattering that is associated with conventional devices and methods. Another potential benefit of the emission modalities described herein is a reduction in the time of a phototherapy treatment and/or the total number of treatments in a regimen to provide a desired effect. The use of both a pulsed emission in combination with either a continuous or periodic emission acts to combat pain and its causes (e.g., inflammation) in a single phototherapy treatment.

Methods of the present invention, using at least two sources of laser energy, can be applied to a wide variety of pathologies and associated tissues of the body where pain or inflammation relief or wound healing is desired. Representative tissues include those of the muscles, tendons, or joints. For example, the methods can be applied to aid wound healing and reduce the development of scar issue after surgical procedures, relieve stiff joints, promote the healing of injured joints, aid in healing fractures and large contusions, reduce edema, reduce pain and inflammation in inflammatory conditions such as arthritis and muscle or tendon injuries, and alleviate or treat musculoskeletal injuries and disorders, including strain and sprain injuries to muscles, tendons, and fascial compartments.

Other conditions which the methods of the invention can alleviate or treat include, but are not limited to, rheumatic disorders, sport traumas, shoulder pain, lesions, ulcers, and bedsores. Particular disorders include, but are not limited to, contusions, hematomas, distortions, muscle strains, lumbago, sciatalgia, myositis, epicondylitis, synovitis, bursitis, and capsulitis. Without being bound by theory, the therapeutic benefits achieved by the inventive methods may stem from various biological mechanisms, acting alone or in combination, which are associated with the ability of chromophores (photoreceptive tissue components) to absorb energy at particular wavelengths or ranges of wavelengths. Such biological mechanisms include, but are not limited to, stimulation of the neurohormone system, activation of cells and cell enzymes (e.g., those associated with the immune and antigen response systems), enhancement of production of adenosine triphosphate (ATP), acceleration of the initial wound healing phase by altering the levels of prostaglandins, acceleration of collagen synthesis, etc. Other possible biological mechanisms associated with phototherapy and other conditions treated thereby are discussed in U.S. Pat. No. 5,445,146, hereby incorporated by reference.

Throughout this disclosure, various aspects are presented in a range format. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 5, from 3 to 6 etc., as well as individual whole and fractional numbers within that range, for example, 1, 2, 2.6, 3, 4, 5, and 6. This applies regardless of the breadth of the range.

In view of the above, it will be seen that several advantages may be achieved and other advantageous results may be obtained. Various changes could be made in the above apparatuses and methods without departing from the scope of the present disclosure. For example, the several (e.g., more than four) laser sources is contemplated, where at least two of these lasers emit energy forms having various characteristics and relationships as described herein. It is intended that all matter contained in this application, including all theoretical mechanisms and/or modes of interaction described above, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLE 1

The effectiveness of phototherapy, using synchronized and spatially overlapping forms of laser energy as described herein, was studied with a sample of 11 patients experiencing knee trauma, characterized by localized pain and/or inflammation. The instrument for delivering the laser energy was capable of use in Multiwave Locked System (MLS) therapy involving the synchronization of different emissions. See Pagnutti, S., *Scientific Report, MLS Therapy*. (September 2004), ASA Srl, Arcugnano, Italy, hereby incorporated by reference. The instrument was also capable of delivering energy from a specified distance from the treatment zone, which could be monitored and controlled using an ultrasound sensor together with robotized movement of the emission head.

An MLS treatment protocol that was programmed in the instrument was selected for use in 10 total phototherapy sessions, administered on consecutive week days. In each session, this protocol delivered a total of 481.5 joules of energy over 10 minutes to a treatment area of approximately 100 cm$^2$ (corresponding to about 4.8 J/cm$^2$). Two laser energy sources were used to deliver this energy, as a combination of a first and second energy forms having wavelengths of 905 nanometers and 808 nanometers, respectively. The emission axes of the laser sources were closely positioned at a distance of 0.4 mm.

The activation periods ($T^1$ and $T^2$) of the first laser energy form, emitted as a train of pulses, and the second laser energy form, emitted periodically, were both 1.43 milliseconds (corresponding to an activation frequency of about 700 Hz). The pulsed and periodic emissions were synchronized, as described herein, by virtue of the simultaneous activation of these emissions. The pulsed energy form was characterized by a pulse duration ($t^1_{pulse}$) of 80 nanoseconds and a pulse period ($T^1_{pulse}$) of 11 microseconds (corresponding to pulse frequency of about 90 kHz at a duty cycle of about 0.73%). The activation time ($t^1_{on}$) of this energy form was 250 microseconds. The activation time of the second energy form ($t^2_{on}$) was 714 microseconds.

A distance of 20 cm between the device and the treatment zone was maintained as consistently as possible throughout each session. The first five treatment sessions involved phototherapy alone, while electrostimulation was added as a co-therapy in the remaining sessions to improve muscle recovery. Not all patients participated beyond the sixth treatment session, as pain treatment therapy was deemed complete in some cases prior to the conclusion of 10 phototherapy sessions.

Figure 8:
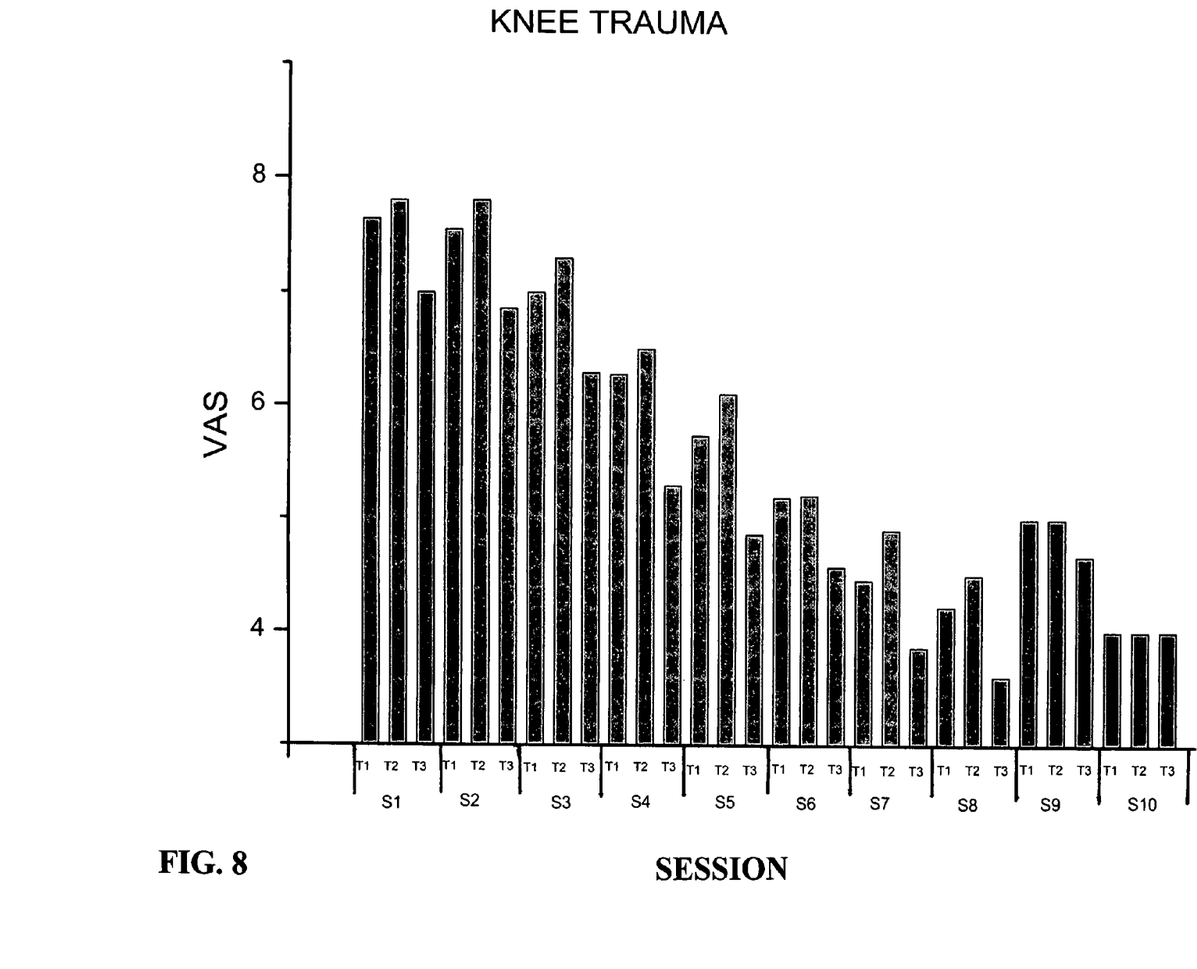
FIG. 8 shows the Visual Analog Scale ("VAS"), a validated measurement of both acute and chronic pain intensity, as a function of the treatment session, over a therapeutic regimen involving 10 total phototherapy sessions for patients experiencing knee trauma. For each session, the VAS was measured before, during, and after laser treatment and the average values among the patients studied are shown at each of these times for all 10 sessions (i.e., resulting in the 30 average VAS measurements shown over time).

At times before, during, and after each treatment session, pain intensity experienced by each patient was evaluated using a Visual Analog Scale (VAS) measurement, which has been validated for the determination of both acute and chronic pain, based on sensory intensity and magnitude. The values of VAS taken "during" each treatment were actually measured upon palpation (i.e., medical examination by touch) of the painful area just prior to the MLS treatment protocol outlined above. A graph of the 30 average VAS measurements (i.e., 3 measurements taken before, during, and after each of 10 sessions) over time as a function of the therapy session is shown in FIG. 8. The VAS values labeled "T1", "T2", and "T3" correspond, respectively, to the measurements "before", "during", and "after" MLS treatment.

The average VAS measurement taken before the first session (S1T1) was about 7.64, with a variance of 3.05. In contrast, the average VAS measurement taken before the seventh session (S7T1) was only about 4.45, with a variance of 7.07. The t-test on these two means gave t=−3.31, and the calculated p value was 0.00345. This further analysis of the data therefore confirmed that the differences between these average VAS values are statistically significant ($p<0.05$). Phototherapy using devices and methods according to the present invention was successful in alleviating pain associated with knee trauma.

EXAMPLE 2

Figure 9:
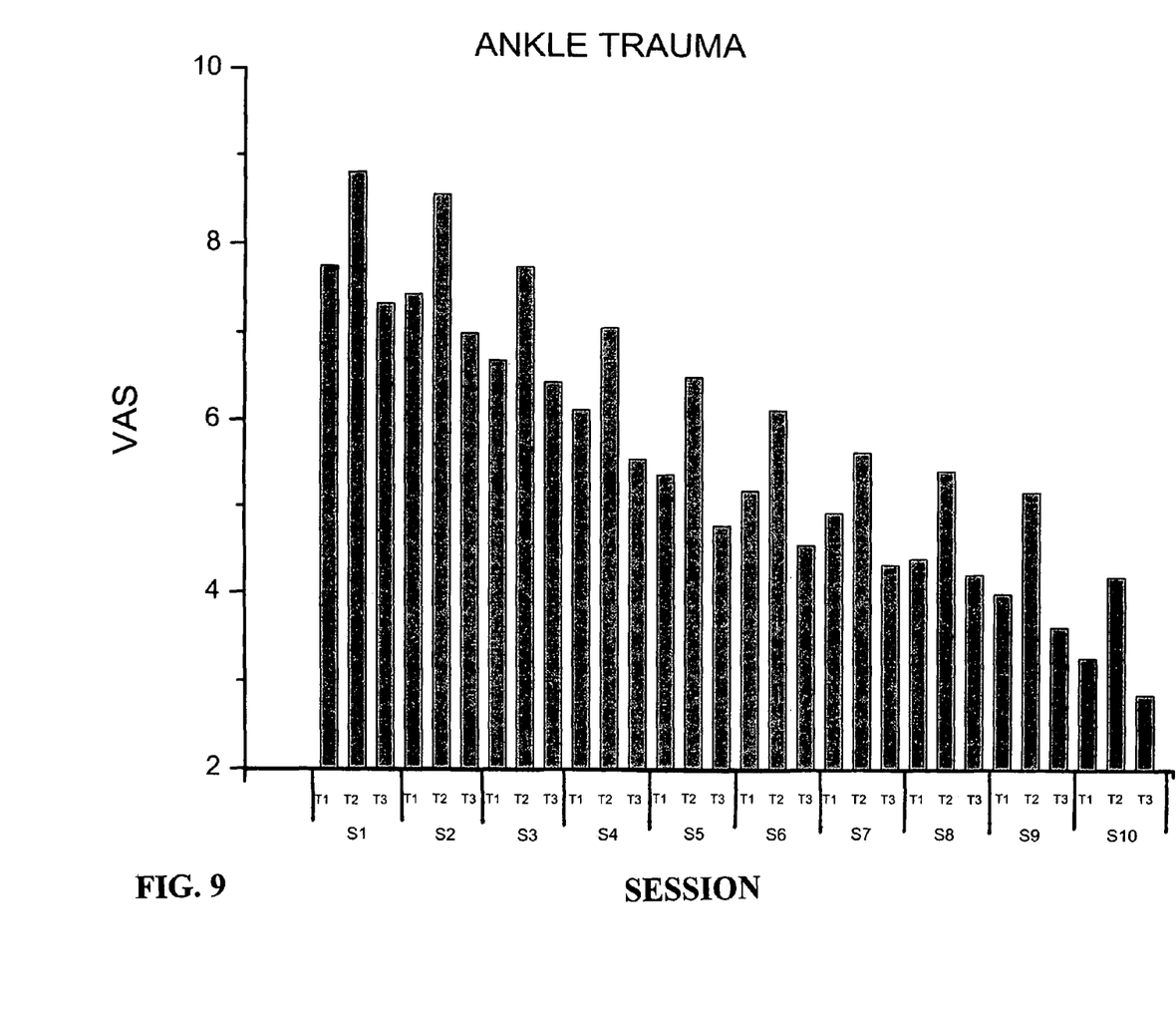
FIG. 9 shows VAS measurements over the course of a phototherapy regimen as described with respect to FIG. 8, but for patients experiencing ankle trauma.

The effectiveness of phototherapy, using synchronized and spatially overlapping forms of laser energy as described herein, was studied again, but in a sample of 16 patients experiencing ankle trauma, characterized by localized pain and/or inflammation. The same instrument for delivering the laser energy, phototherapy treatment protocol, and treatment regimen (with 10 sessions on consecutive week days) were used as described in Example 1. A graph of the 30 average VAS measurements (i.e., 3 measurements taken before, during, and after each of 10 sessions) over time as a function of the therapy session is shown in FIG. 9.

The average VAS measurement taken before the first session (S1T1) was about 7.75, with a variance of 2.20. In contrast, the average VAS measurement taken before the sixth session (S6T1) was only about 5.19, with a variance of 3.63. The t-test on these two means gave t=−4.25, and the calculated p value was 0.000194. This further analysis of this data therefore confirmed that the differences between these average VAS values are statistically significant ($p<0.05$). Phototherapy using devices and methods according to the present invention was successful in alleviating pain associated with ankle trauma.

What is claimed is:

1. A method for delivering laser energy to a treatment zone of tissue targeted for phototherapy, wherein the treatment zone of tissue has a cross-sectional surface treatment area, the method comprising
   a) providing a laser emitting device including at least two separate laser sources with each one emitting energy sufficient to treat the tissue, wherein a first separate laser source emits through a first emission beam a first laser energy form having a first wavelength between 600 nm and 1100 nm and a first power between 10 watts and 100 watts, wherein a second separate laser source emits through a second emission beam a second laser energy form having a second wavelength between 600 nm and 1100 nm and a second power between 1 watt and 6 watts, wherein each of the first and second emission beams have a corresponding emission axis, and wherein the at least two separate laser sources are positioned in close proximity with the emission axes spaced apart by at most 1 mm, so that the emission beams overlap over most of the length from the region of emission from the laser sources to the region of the treatment area
   b) simultaneously applying to the treatment area the first laser energy form and the second laser energy form;
   c) synchronizing the laser emitting device such that the laser energy applied simultaneously by the at least two separate laser sources to the treatment area is between 1 mW/cm² and 25 mW/cm².

2. The method of claim 1, wherein said emission axes are separated by at most about 0.5 mm.

3. The method of claim 1, wherein said emission axes are separated by at most about 0.2 mm.

4. The method of claim 1, wherein said first and second laser energy forms spatially overlap over at least about 90% of said lengths of one or both of said emission axes.

5. The method of claim 1, wherein said first laser energy form is applied periodically with a first activation time ($t^1on$) and a first activation period ($T^1$), to said treatment zone, wherein, over said first activation time ($t^1on$), a plurality of laser energy pulses are applied with a pulse duration ($t^1pulse$) and a pulse period ($T^1pulse$).

6. The method of claim 5, wherein said first activation time ($t^1on$) is from about 100 to about 1000 microseconds.

7. The method of claim 5, wherein said pulse duration ($t^1pulse$) is from about 5 to about 500 nanoseconds.

8. The method of claim 5, wherein said pulse period ($T^1pulse$) is from about 5 to about 500 microseconds.

9. The method of claim 5, wherein said second laser energy form is emitted continuously.

10. The method of claim 5, wherein said second laser energy form is emitted periodically with a second activation time ($t^2on$) and a second activation period ($T^2$).

11. The method of claim 10, wherein said first activation period ($T^1$) and said second activation period ($T^2$) are equal or substantially equal.

12. The method of claim 11, wherein said first activation time ($t^1on$) and said second activation time ($t^2_{on}$) begin simultaneously or substantially simultaneously.

13. The method of claim 1 wherein the first laser energy form has a wavelength from about 800 to about 1000 nanometers; and wherein the second laser energy form has a wavelength from about 700 to about 1100 nanometers.

14. The method of claim 1 wherein the wavelength of the first laser energy form is 905 nanometers and the wavelength of the second laser energy form is 808 nanometers.

15. A method for alleviating or treating a condition characterized by pain, inflammation, or edema of a tissue, the method comprising simultaneously exposing said tissue in a treatment area to a first laser energy form having a first wavelength between 600 nm and 1100 nm and a first power between 10 watts and 100 watts sufficient to treat tissue in the treatment area and a second laser energy form having a second wavelength between 600 nm and 1100 nm and a second power between 1 watt and 6 watts sufficient to treat tissue in the treatment zone, wherein said first laser energy form and said second laser energy form have emission axes that are separated by at most about 1 mm and provide laser energy to the treatment area between 1 mW/cm² and 25 mW/cm².

16. The method of claim 15, wherein said first and second laser energy forms spatially overlap over most of the length of one or both of said emission axes.

17. The method of claim 15, wherein said first laser energy form is periodic and has a first activation time ($t^1_{on}$) and a first activation period ($T^1$), and wherein, over said first activation time ($t^1on$), a plurality of laser energy pulses are emitted with a pulse duration ($t^1on$) and a pulse period ($T^1pulse$).

18. The method of claim 15, wherein said tissue comprises a tendon or a muscle.

19. The method of claim 15, wherein said condition is a rheumatic disorder, a sport trauma, shoulder pain, or a lesion.

20. The method of claim 15, wherein said condition is selected from the group consisting of a contusion, a hematoma, a distortion, a muscle strain, lumbago, sciatalgia, myositis, epicondylitis, synovitis, bursitis, and capsulitis.

21. The method of claim 15 wherein the first laser energy form has a wavelength from about 800 to about 1000 nanometers; and wherein the second laser energy form has a wavelength from about 700 to about 1100 nanometers.

22. The method of claim 15 wherein the wavelength of the first laser energy form is 905 nanometers and the wavelength of the second laser energy form is 808 nanometers.

* * * * *